US00PP30763P3

(12) United States Plant Patent
Wood

(10) Patent No.: US PP30,763 P3
(45) Date of Patent: Jul. 30, 2019

(54) ***HEPTACODIUM MICONIOIDES* PLANT NAMED 'SMNHMRF'**

(50) Latin Name: *Heptacodium miconioides*
Varietal Denomination: SMNHMRF

(71) Applicant: Timothy Wood, Spring Lake, MI (US)

(72) Inventor: Timothy Wood, Spring Lake, MI (US)

(73) Assignee: Spring Meadow Nursery, Inc., Grand Haven, MI (US)

( * ) Notice: Subject to any disclaimer, the term of this patent is extended or adjusted under 35 U.S.C. 154(b) by 0 days.

(21) Appl. No.: 15/732,604

(22) Filed: Nov. 30, 2017

(65) Prior Publication Data

US 2019/0166745 P1 May 30, 2019

(51) Int. Cl.

| | |
|---|---|
| ***A01H 6/00*** | (2018.01) |
| ***A01H 5/00*** | (2018.01) |
| ***A01H 5/02*** | (2018.01) |

(52) U.S. Cl.
USPC ..... Plt./216
CPC ..... *A01H 6/00* (2018.05); *A01H 5/02* (2013.01)

(58) Field of Classification Search
USPC ..... Plt./216, 226
CPC ..... A01H 5/00; A01H 6/00
See application file for complete search history.

*Primary Examiner* — Keith O. Robinson
(74) *Attorney, Agent, or Firm* — Cassandra Bright

(57) ABSTRACT

A new and distinct *Heptacodium* cultivar named 'SMNHMRF' is disclosed, characterized by early blooming and compact plants. Sepals are ornamental, elongating in the Fall, and turning bright red. The new variety is a *Heptacodium*, normally used for outdoor ornamental purposes as a large shrub or small tree.

3 Drawing Sheets

Latin name of the genus and species: *Heptacodium miconioides.*

Variety denomination: 'SMNHMRF'.

BACKGROUND OF THE INVENTION

The new cultivar is a product of a planned breeding program. The new variety was discovered as the result of a planned mutation breeding program. Unnamed, unpatented *Heptacodium miconioides* were treated with an x-ray treatment. The treated plant material was grown out and observed for commercially interesting characteristics. The inventor discovered the new variety in 2008 at a commercial nursery in Grand Haven, Mich.

Asexual reproduction of the new cultivar 'SMNHMRF' was first performed during 2013 at a commercial nursery in Grand Haven, Mich. by softwood cuttings. Subsequent propagation of three generations has shown that the unique features of this cultivar are stable and have been reproduced true to type in successive generations.

SUMMARY OF THE INVENTION

The cultivar 'SMNHMRF' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'SMNHMRF' grown in Grand Haven, Mich. These characteristics in combination distinguish 'SMNHMRF' as a new and distinct *Heptacodium miconioides* cultivar:

1. Early blooming.
2. Showy blooms.

3. Compact plant form.
4. Large, colorful bracts.

PARENT COMPARISON

Plants of the new cultivar 'SMNHMRF' are similar to plants of the parent in most horticultural characteristics, however, plants of the new cultivar 'SMNHMRF' differ in the following;

1. Bracts of the new variety turn vibrant red, bracts of the parent variety are blush pink to pale red.
2. Plants of the new variety are more compact than plants of the parent variety.
3. The new variety produces larger inflorescence than plants of the parent variety.

COMMERCIAL COMPARISON

The inventor is not aware of other commercial varieties or *Heptacodium* species to compare with.

BRIEF DESCRIPTION OF THE PHOTOGRAPHS

The accompanying photograph in FIG. 1 illustrates in full color a typical plant of 'SMNHMRF' in Grand Haven, Mich., during Summer. Age of the plant in FIG. 1 is approximately 3 years.

Figure 1:
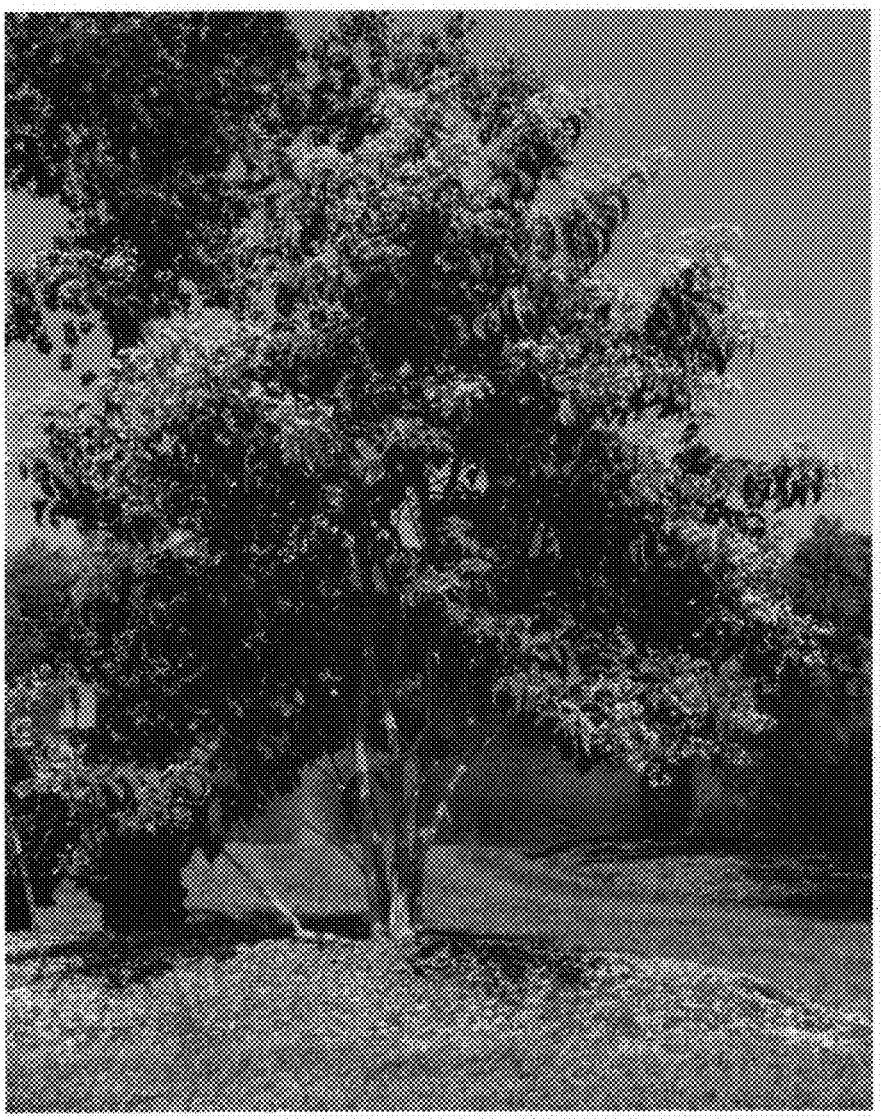
Figure 2:
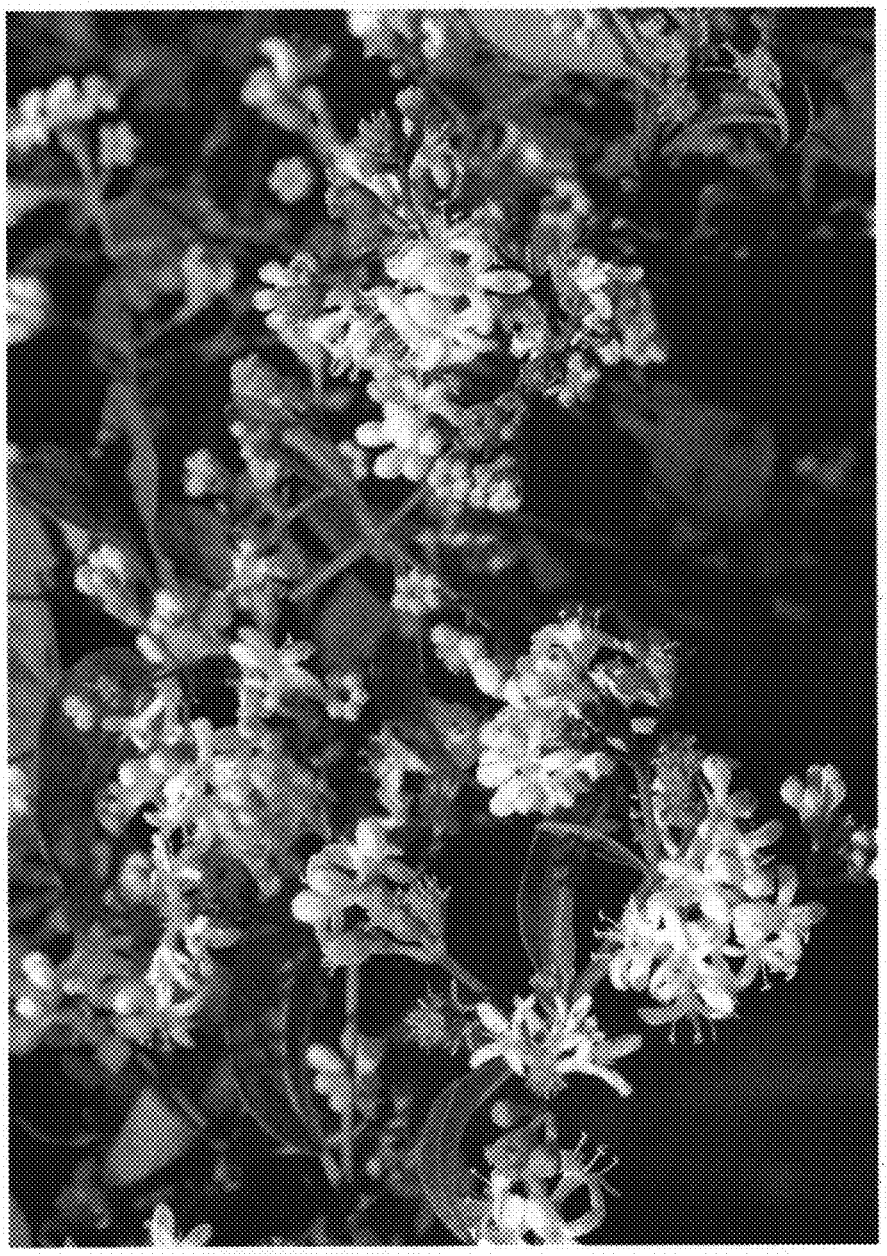
FIG. 2 illustrates flowers of 'SMNHMRF'.
Figure 3:
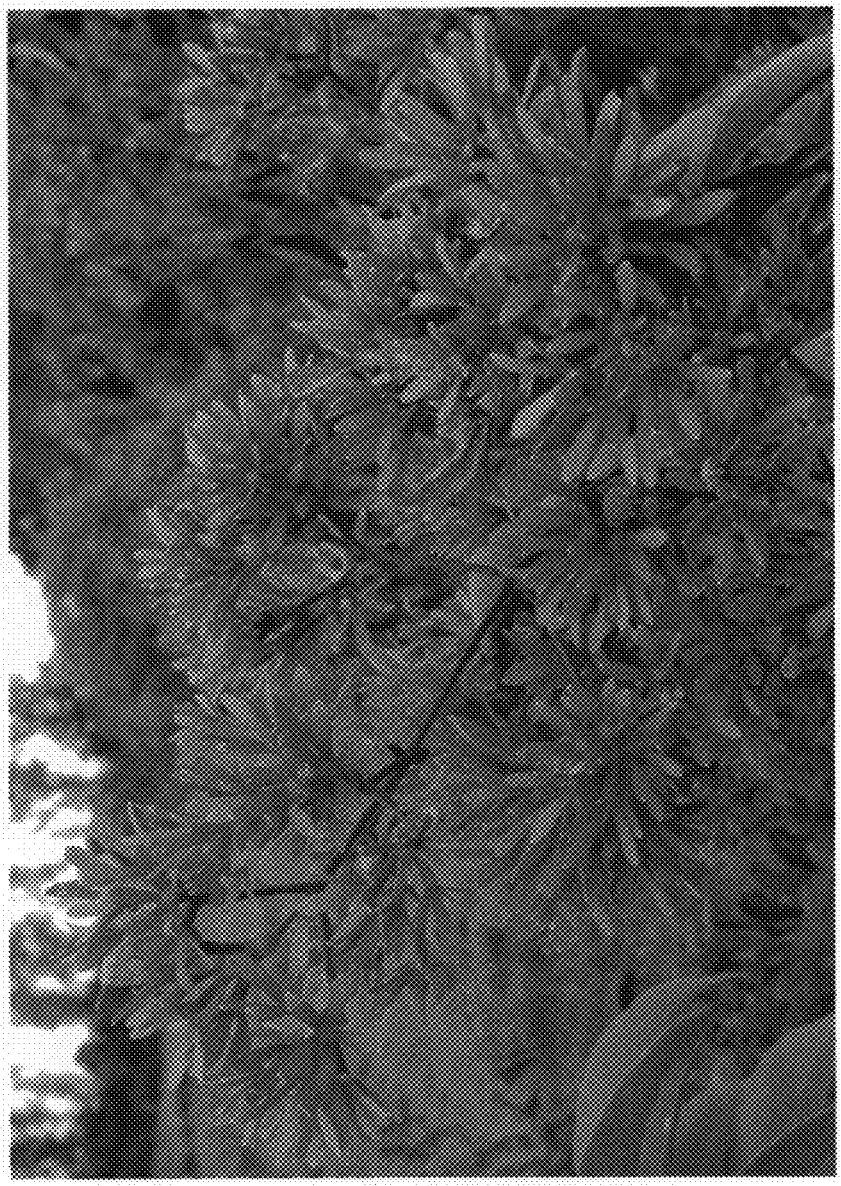
FIG. 3 illustrates calyces in the Fall.

The photographs were taken using conventional techniques and although colors may appear different from actual colors due to light reflectance it is as accurate as possible by conventional photographic techniques.

DETAILED BOTANICAL DESCRIPTION

In the following description, color references are made to The 2015 Royal Horticultural Society Colour Chart except where general terms of ordinary dictionary significance are used. The following observations and measurements describe 2-year-old 'SMNHSDD' plants grown in a poly greenhouse, in Grand Haven, Mich., USA. The growing temperature ranged from approximately 18° C. to 27° C. daytime and 5° to 10° C. at night. Measurements and numerical values represent averages of typical plant types. Measurements were taken during August of 2017.

Botanical classification: *Heptacodium miconioides* 'SMNHMRF'.

PROPAGATION

Typical method: Softwood cuttings.
Time to initiate roots: About 30 days at 18° to 27° C.
Time to produce a young plant: About 2 to 3 months at 18 to 27 deg. C.
Root description: Woody. Brown roots not accurately measured with an R.H.S. chart.

PLANT

Growth habit: Perennial shrub or small tree.
Commercial size pots: 2, 3 and 5 gallon.
Height: 122 cm.
Spread: 92 cm.
Growth rate: Moderate.
Lateral branch characteristics:
- *Quantity*.—Average 11.
- *Length*.—Average 41 cm.
- *Diameter*.—Average 3.5 mm.
- *Shape in cross-section*.—Round.
- *Texture*.—Non-pubescent, no lenticels.
- *Aspect and angle*.—5° to 90° from center of plant.
- *Color*.—Upper surface near Greyed-Orange 166B. Lower surface near Yellow-Green 145B.

FOLIAGE

Leaf:
- *Arrangement*.—Opposite, single.
- *Average length*.—Approximately 10 cm.
- *Average width*.—Approximately 4 cm.
- *Shape of blade*.—Asymmetrical broad deltate.
- *Apex*.—Aristate to acuminate.
- *Base*.—Obtuse.
- *Margin*.—Entire, ciliate.
- *Texture of top surface*.—Dusty, slightly rough.
- *Texture of lower surface*.—Glabrous with distinct veins. Pubescent on mid rib.
- *Color*.—Young foliage: Upper side: Near RHS Green 143A. Under side: Near RHS Green 138B. Mature foliage: Upper side: Near RHS Green 143A. Under side: Near RHS Green 138B. Mature Fall foliage: Upper side: Near RHS Green 143A. Under side: Near RHS Green 138B.

Foliage:
- *Venation*.—Type: Palmate. Color: Venation color upper side: Near RHS Yellow-Green 153D. Venation color under side: Near RHS Yellow-Green 150D. Petiole: Length: Average 1.0 cm. Diameter: Average 2.5 mm. Texture: Pubescent upper and lower surfaces. Color: Upper side: Near Greyed-Orange 168A. Under side: Near RHS Yellow-Green 145C.

FLOWER

Natural flowering season: Late Summer to Fall.
Inflorescence form: Panicles.
Flowers per inflorescence: Average 30, with about 50 unopened buds.
Inflorescence size:
- *Width*.—32 cm.
- *Height*.—27 cm.

Individual flowers:
- *Type*.—Single, rotate.
- *Aspect*.—Flowers face all directions, outward and upward, also downward, but not drooping.
- *Diameter*.—1.0 cm.
- *Length*.—1.5 cm.
- *Persistence*.—Self-cleaning.
- *Fragrance*.—Sweet, mildly intense.

Petals:
- *Arrangement*.—Whorled.
- *Number*.—5.
- *Shape*.—Near linear.
- *Margin*.—Entire.
- *Tip shape*.—Rounded.
- *Base shape*.—Truncate, unfused.
- *Length*.—Average 7 mm.
- *Width*.—Average 3 mm.
- *Texture*.—Upper: Soft, smooth, delicate. Lower: Soft, smooth, delicate.
- *Color*.—When opening: Upper surface: White N155D. Under surface: White N155D. Fully opened: Upper surface: White N155D. Under surface: White N155D. Fading: Upper surface: White N155D. Under surface: White N155D.

Bud:
- *Shape*.—Obovate.
- *Length*.—1 cm.
- *Diameter*.—5 mm.
- *Color*.—Near White 155B.

Sepals:
- *Development*.—Very small and inconspicuous until Fall, then elongating and changing color.
- *Arrangement*.—Whorl.
- *Shape*.—Narrowly triangular.
- *Tip shape*.—Acute.
- *Base shape*.—Truncate.
- *Margin*.—Entire.
- *Quantity per flower*.—6.
- *Length*.—Spring/Summer: 1 mm. Fall: 1 cm.
- *Width*.—Spring/Summer: 1 mm. Fall: 3 mm.
- *Texture*.—Upper: Smooth. Lower: Smooth.
- *Color*.—Upper: Spring/Summer: Yellow-Green 145B. Fall: Red-Purple 60C. Lower: Spring/Summer: Yellow-Green 145B. Fall: Red-Purple 60C.

Peduncle:
- *Length*.—3 mm.
- *Diameter*.—2 mm.
- *Texture*.—Smooth.
- *Color*.—Yellow-Green 145B.
- *Orientation*.—Upright and outward at angles between 0 to 40 degrees.
- *Strength*.—Strong.

Pedicel: Not present.

REPRODUCTIVE ORGANS

Stamens:
*Number*.—About 5.
*Filament length*.—5 mm.
*Filament color*.—White N155D.
Anthers:
*Shape*.—Club-shaped.
*Length*.—1 mm.
*Color*.—Brown N200A.
*Pollen*.—Amount: Scant. Color: Greyed-Yellow 160B.
Pistil:
*Number*.—1.
*Length*.—3 mm.
*Style*.—Length: 5 mm. Color: White N155D.
Stigma:
*Shape*.—Globular.
*Color*.—White N155D.
*Ovary color*.—White N155D.

OTHER CHARACTERISTICS

Fruits and seeds: Not observed to date.
Disease/pest resistance: Neither resistance nor susceptibility to normal diseases and pests of *Heptacodium* observed.
Temperature tolerance: Observed to tolerate high temperatures, to 36° C. and low temperatures to at least −32° C.

What is claimed is:

1. A new and distinct cultivar of *Heptacodium* plant named 'SMNHMRF' as herein illustrated and described.

* * * * *